(12) United States Patent
Wang-Lee

(10) Patent No.: US 7,725,959 B2
(45) Date of Patent: Jun. 1, 2010

(54) PROTECTIVE GOGGLES

(75) Inventor: Tzu-Feng Wang-Lee, Tainan (TW)

(73) Assignee: Jiann Lih Optical Co., Ltd., Tainan County (TW)

( * ) Notice: Subject to any disclaimer, the term of this patent is extended or adjusted under 35 U.S.C. 154(b) by 384 days.

(21) Appl. No.: 11/758,891

(22) Filed: Jun. 6, 2007

(65) Prior Publication Data

US 2008/0301857 A1    Dec. 11, 2008

(51) Int. Cl.
*A61F 9/02*    (2006.01)
(52) U.S. Cl. ......................................................... 2/428
(58) Field of Classification Search .................... 2/426, 2/428, 448
See application file for complete search history.

(56) References Cited

U.S. PATENT DOCUMENTS

| | | | |
|---|---|---|---|
| 5,617,588 A | 4/1997 | Canavan et al. ................. | 2/428 |
| 6,276,795 B1 * | 8/2001 | Hall et al. ...................... | 351/62 |
| 6,948,813 B2 * | 9/2005 | Parks ........................... | 351/158 |
| 7,343,631 B2 * | 3/2008 | Lin ............................... | 2/448 |

* cited by examiner

*Primary Examiner*—Katherine Moran
(74) *Attorney, Agent, or Firm*—Alan Kamrath; Kamrath & Associates PA

(57) ABSTRACT

Protective goggles have an integrally formed lens, a frame and a strap. The lens has an opening formed on an upper side for engaging with an engaging portion on an upper side of a frame with a soft protective pad and has a protrusion extending upwardly from a middle section of a lower side to be inserted into a hole adjacent to a concave section formed on a lower side of the frame. More than one rib is provided on an upper side of the frame for fitting with the lens and for stably propping the lens. A through hole is provided on each end of the frame and has raised portions projected therearound for passing through a through hole of the lens. A tenon is formed adjacent each through hole of the fence for passing through an aperture of the lens. The lens and the frame are coupled by buckles combined with both ends of the strap.

1 Claim, 4 Drawing Sheets

PROTECTIVE GOGGLES

FIELD OF THE INVENTION

The present invention relates to an assembly for protective goggles. Particularly, the present invention relates to an assembly of protective goggles combining integrally formed lens with a frame with a strap such that the goggles for sport use can be easily implemented through an easy assembling operation.

BACKGROUND OF THE INVENTION

A variety of conventional eyeglasses include those for vision correction and those for sport purposes as well as those for protecting eyes from being hurt by strong external light. Users may select an appropriate kind among these eyeglass assemblies with different purposes in accordance with their needs. The present invention improves the eyeglass assembly for sport purposes, utilizing the eyeglass assembly of the kind which combines integrally formed lens with a protective frame and which has a strap at two ends of the protective frame that can be comfortably fitted with a head of a user.

SUMMARY OF THE INVENTION

The present invention improves the conventional sport goggle assembly into a different assembly through combining a frame and an integrally formed lens with a strap at two ends such that the assembly and manufacture of components can be more easily implemented.

One aspect of the present invention is to provide a pair of protective goggles having an integrally formed lens, a frame with a protective pad formed of a soft material and a strap with buckles combined with both ends. The lens has an opening formed at a middle section of an upper side for correspondingly engaging with an engaging portion on an upper side of the frame. A protrusion extends upwardly from an inner surface of a nose supporting portion at a lower side to be correspondingly inserted into a hole adjacent to a concave section formed on a middle section of a lower side of the frame for positional restriction. A through hole is formed on each end of the lens, and an aperture is located adjacent to each through hole. The frame Farther has more than one rib provided on the upper side for correspondingly fitting with the lens and for stably propping the lens. A through hole is provided on each end of the frame, with raised portions projected around each through hole for passing through the corresponding through hole of the lens. A tenon is formed adjacent each through hole of the frame for passing through the corresponding aperture of the lens. Each buckle combined with each end of the strap has an engaging section subsequently passing through the through holes of the lens and the frame. A boundary portion formed at an open end of the engaging section is rotated in a direction so as to stably lean against an inner surface of the through holes of the frame. As a result, easy assembling and stable combination for the protective goggles are achieved.

DETAILED DESCRIPTION OF THE EMBODIMENTS

Figure 2:
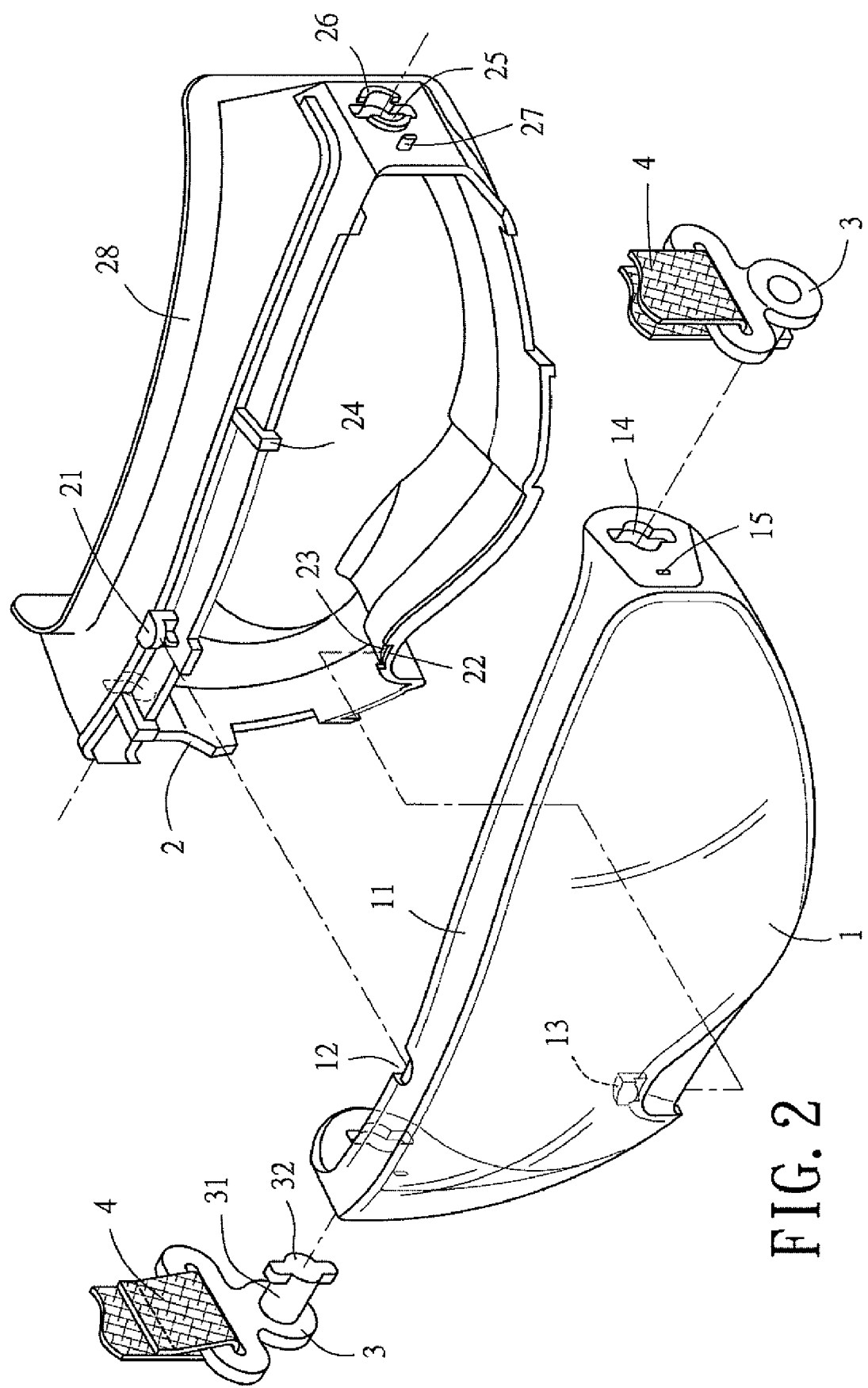
FIG. 2 is an exploded view of the protective goggles in accordance with the present invention.

Referring to FIG. 2, a pair of protective goggles 5 in accordance with the present invention include an integrally formed lens 1, a frame 2 and a strap 4 having two ends respectively connected to buckles 3.

The lens 1 is formed of hard material having an integral covering edge 11 extending backward from a periphery thereof, an opening 12 formed at a middle section of an upper side, a protrusion 13 extending upwardly from an inner surface of a nose supporting portion at a lower side, through holes 14 provided on two ends respectively, and apertures 15 adjacent to respective through holes 14.

The frame 2 has a protective pad 28 integrally formed of a softer plastic material on the back and is shaped to the periphery of the lens 1. The frame 2 has an engaging portion 21 provided on a middle section of an upper side, a hole 23 provided adjacent to a concave section 22 formed on a middle section of an lower side, more than one rib 24 provided on the upper side, and through holes 25 respectively provided on left and right ends. Each through hole 25 has raised portions 26 projected from a periphery thereof and a tenon 27 formed adjacently.

The strap 4 has two ends respectively combined with buckles 3 each having an engaging section 31 extending from one side thereof. The engaging section 31 is formed with a boundary portion 32 at an open end.

Figure 1:
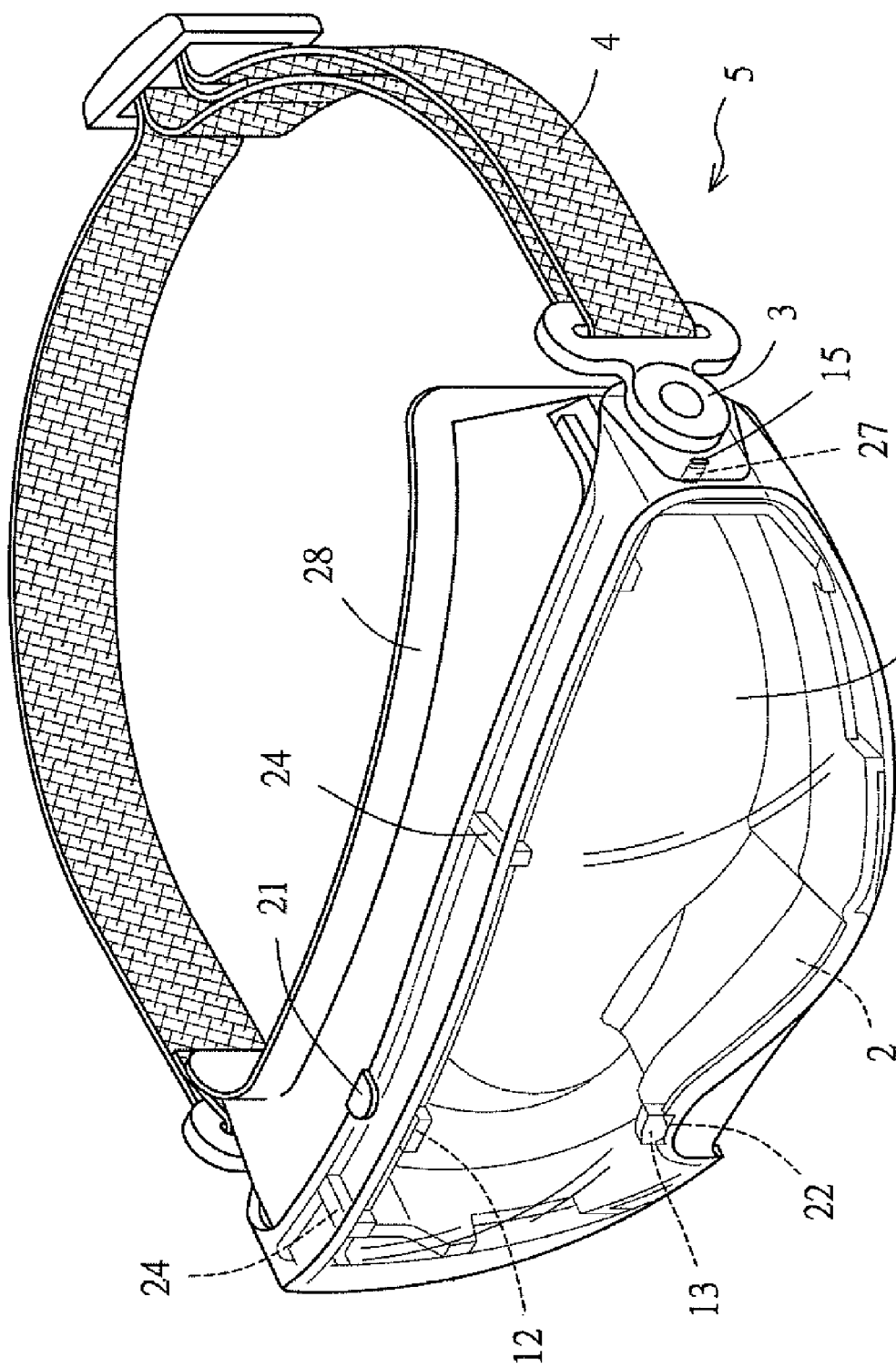
FIG. 1 is a perspective view of assembled protective goggles in accordance with the present invention.
Figure 3:
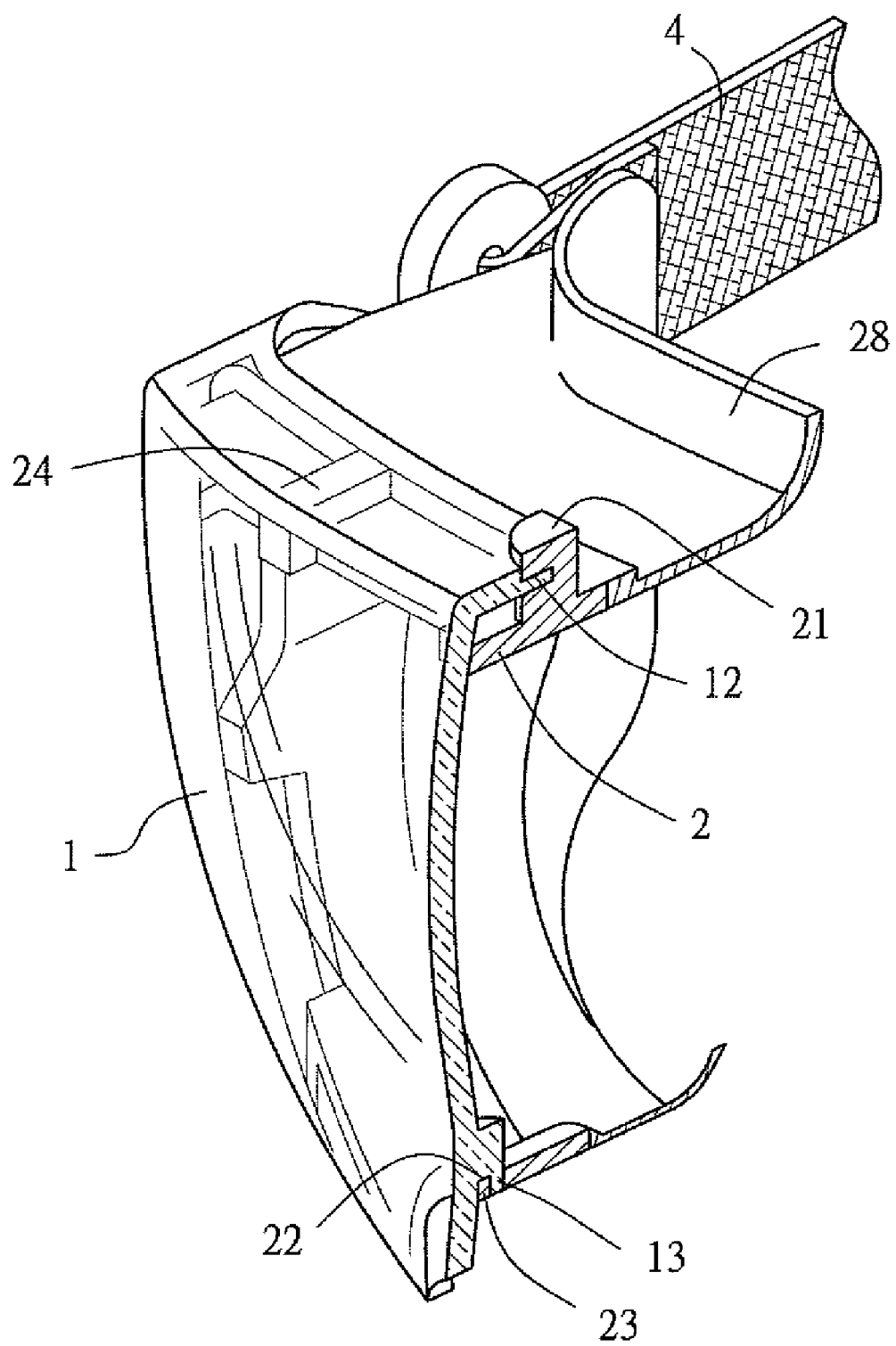
FIG. 3 is a cross-sectional schematic view of the assembly of a lens and an frame in accordance with the present invention.
Figure 4:
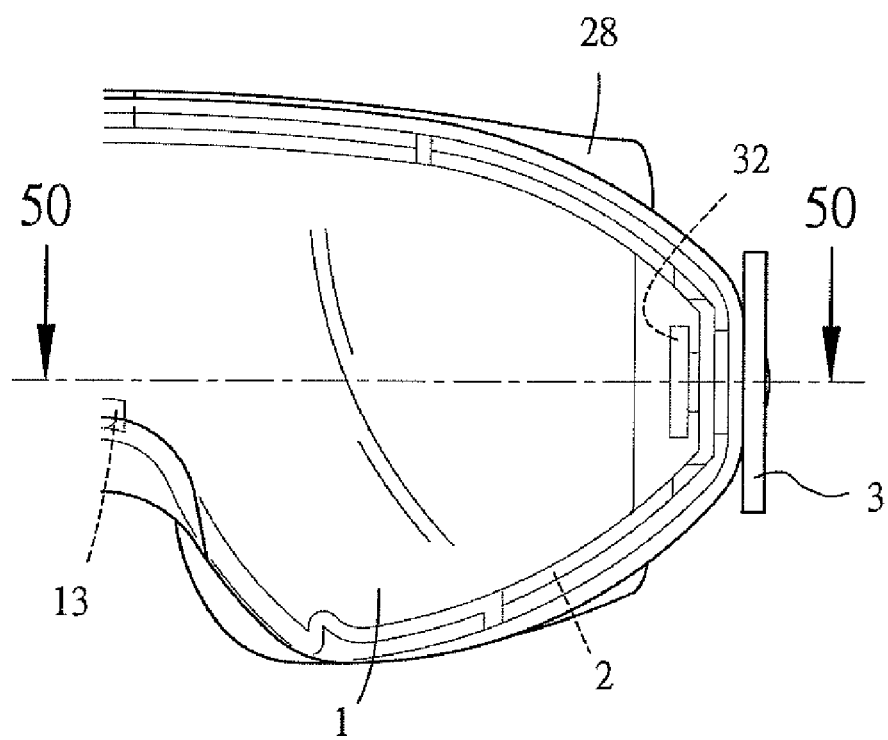
FIG. 4 is a frontal view of the eyeglass lens, the frame and a strap with buckles in accordance with the present invention.
Figure 5:
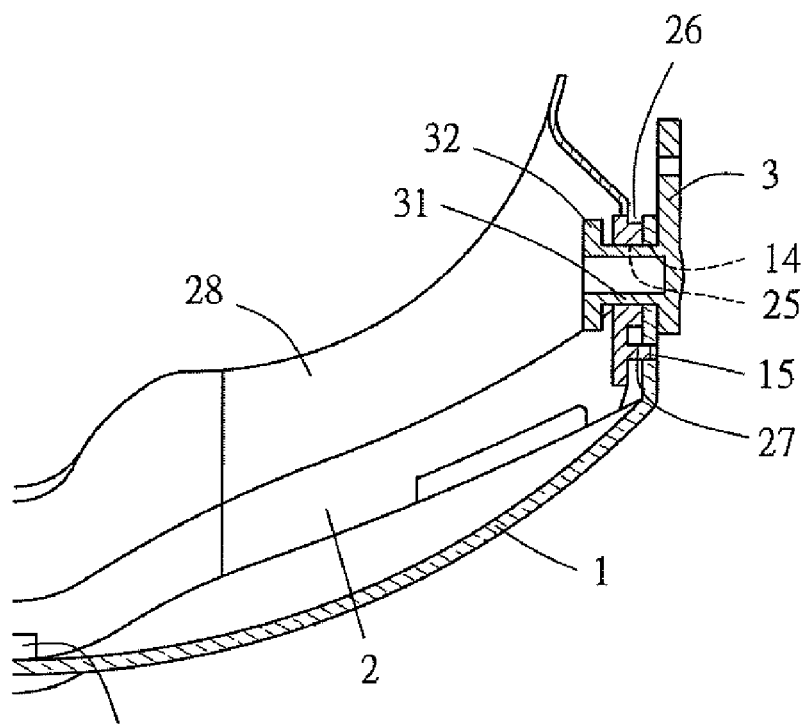
FIG. 5 is a top cross-sectional view of taken along line 50-50 of FIG. 4.

FIG. 3 illustrates assembling of the integrally formed lens 1, the frame 2 and the strap 4 with the buckle 3 on the two ends. The frame 2 is correspondingly fitted in the covering edge 11 extending from the periphery of the lens 1 such that the engaging portion 21 on the upper side of the frame 2 engages with the opening 12 of the lens 1. The protrusion 13 of the lens 1 is correspondingly inserted into the hole 23 adjacent to the concave section 22 formed on the middle section of the lower side of the frame 2, as shown in FIG. 1. An inner surface of the cover edge 11 of the lens 1 is stably propped against the rib 24 on the upper side of the frame 2, as shown in FIG. 3. Each of the through holes 25 of the frame 2 is then aligned with the corresponding through holes 14 of the lens 1. As shown in FIGS. 4, 5, the raised portions 26 around the through hole 25 project from the through hole 14, and the tenon 27 adjacent to the raised portions 26 passing into the aperture 15 of the lens 1. Finally, the boundary portion 32 formed at the open end of the engaging section 31 of each buckle 3 combined with each end of the strap 4 subsequently passes through each through hole 14 of the lens 1 and each through bole 25 of the frame 2. The buckles 3 are rotated at an angle, such as 90°, so that the boundary portions 32 of the engaging sections 31 is stably against an inner surface of the through holes 25 of the frame 2, as shown in FIG. 4. As a result, the integrally formed lens 1, the frame 2 and the strap 4 combined with the buckles 3 can be easily assembled into the stable protective goggles 5, as shown in FIG. 1.

The protective goggles for sport purposes in accordance with the present invention have the following advantages:

1. The integrally formed lens and the frame are combined through engaging the upper and lower sides of the lens and the frame so as to obtain a stable combination between the two elements and so that disassembly of the two element can be implemented easily; and 2. The assembly of the lens and the frame is further assembled with the buckles at the two ends of the strap with each engaging section of the buckle passing through the through holes of the lens and the frame and with the buckle rotated, until the boundary portion of the engaging section is stably against an inner surface of the frame, thereby achieving easily stable combination and fast disassembly for the protective goggles.

What is claimed is:

1. A pair of protective goggles comprising:
   a lens having a periphery;
   an integral covering integrally extending backward from the lens;
   a frame shaped to the periphery of the lens and having a protective pad made of soft materials; and
   a strap having two ends each connected to a buckle;
   wherein the integral covering of the lens has an opening formed at a middle section of an upper side for correspondingly engaging with an engaging portion on an upper side of the frame, a protrusion extending upwardly from an inner surface of a nose supporting portion at a lower side to be correspondingly inserted into a hole adjacent to a concave section formed on a middle section of a lower side of the frame for positional restriction, a through hole formed on each end and an aperture adjacent to each though hole;
   wherein the frame further has more than one rib extending on the upper side and correspondingly fitting with the lens and extending on a front side and stably propping the lens, a through hole provided on each end with a raised portion projected therearound and a tenon formed adjacent to the raised portion and passing through the corresponding aperture of the lens, with the raised portion projecting through the corresponding through hole of the integral covering of the lens; and
   wherein each buckle combined with each end of the strap has an engaging section subsequently passing through the raised portion and the through holes of the integral covering of the lens and the frame, and a boundary portion formed at an open end of the engaging section rotated at a direction so as to stably lean against an inner surface of the through hole of the frame; whereby protective goggles with easy assembling and stable combination are achieved.

* * * * *